United States Patent [19]

Yang et al.

[11] Patent Number: 5,424,289
[45] Date of Patent: Jun. 13, 1995

[54] SOLID FORMULATIONS OF THERAPEUTIC PROTEINS FOR GASTROINTESTINAL DELIVERY

[75] Inventors: Heechung Yang, Palo Alto; Vu A. Nguyen, San Jose; Liang C. Dong, Mountain View; Patrick S.-L. Wong, Palo Alto, all of Calif.

[73] Assignee: Alza Corporation, Palo Alto, Calif.

[21] Appl. No.: 99,884

[22] Filed: Jul. 30, 1993

[51] Int. Cl.$^6$ ............................................. A61K 38/00
[52] U.S. Cl. ........................................ 514/12; 514/3; 530/303; 530/324; 530/399; 424/409; 424/465; 424/498
[58] Field of Search ..................... 514/3, 14, 12, 21, 2, 514/3

[56] References Cited

U.S. PATENT DOCUMENTS

| | | | |
|---|---|---|---|
| 3,950,521 | 4/1976 | Higuchi | 514/162 |
| 4,639,435 | 1/1987 | Fujii | 514/11 |
| 4,702,918 | 10/1987 | Ushimaru | 514/60 |

FOREIGN PATENT DOCUMENTS

| | | | |
|---|---|---|---|
| 0036145 | 9/1981 | European Pat. Off. | A61K 31/62 |
| 0036534 | 9/1981 | European Pat. Off. | A61K 31/62 |
| 0067513 | 12/1982 | European Pat. Off. | A61K 37/43 |
| 0177342 | 9/1986 | European Pat. Off. | A61K 37/36 |
| 0053412 | 3/1982 | Japan . | |

OTHER PUBLICATIONS

Illustrated Stedman's Medical Dictionary, 24th ed., Williams and Wilkin's, Los Angeles, 1982, p. 421.

Moore, et al., International Journal of Pharmaceutics, 34 (1986) pp. 35–43, "Absorption Enhancement of Growth Hormone from the Gastrointestinal Tract of Rats".

Palin, et al., J. Pharm. Pharmacol, 1982, vol. 34, pp. 707–710, "The Effect of Oils on the Lymphatic Absorption of DDT".

Palin, et al., J. Pharm. Pharmacol, 1984, vol. 36, pp. 641–643, "The Effect of Different Oils on the Absorption of Probucol in the Rat".

Omran, et al., Pharm. Acta Helv., vol. 58, No. 8 (1983), pp. 237–140, "Bioavailability Studies on an Orally Administered, Oily Suspension of a Water Soluble Drug".

*Primary Examiner*—Jill Warden
*Assistant Examiner*—David Lukton
*Attorney, Agent, or Firm*—Paul L. Sabatine; Jacqueline S. Larson; Edward L. Mandell

[57] ABSTRACT

The present invention is directed to a pharmaceutical formulation of a therapeutic polypeptide together with a permeation-enhancing mixture of sodium salicylate and an oil to provide enhanced absorption of the polypeptide through the wall of the gastrointestinal tract, and particularly of the colon, after oral administration, the amount of oil being from about 10 wt % to about 30 wt %, preferably from about 15 wt % to about 25 wt %, of the total formulation and the amount of sodium salicylate being from about 70 wt % to about 90 wt %, preferably from about 75 wt % to about 85 wt %, of the total formulation. The polypeptide may be non-lyophilized. The pharmaceutical formulation is characterized as a solid, which provides a convenient and improved format for handling and storage and for the preparation of oral dosage forms (such as pills, capsules and delivery vessels) containing a homogeneous mixture of ingredients.

4 Claims, 3 Drawing Sheets

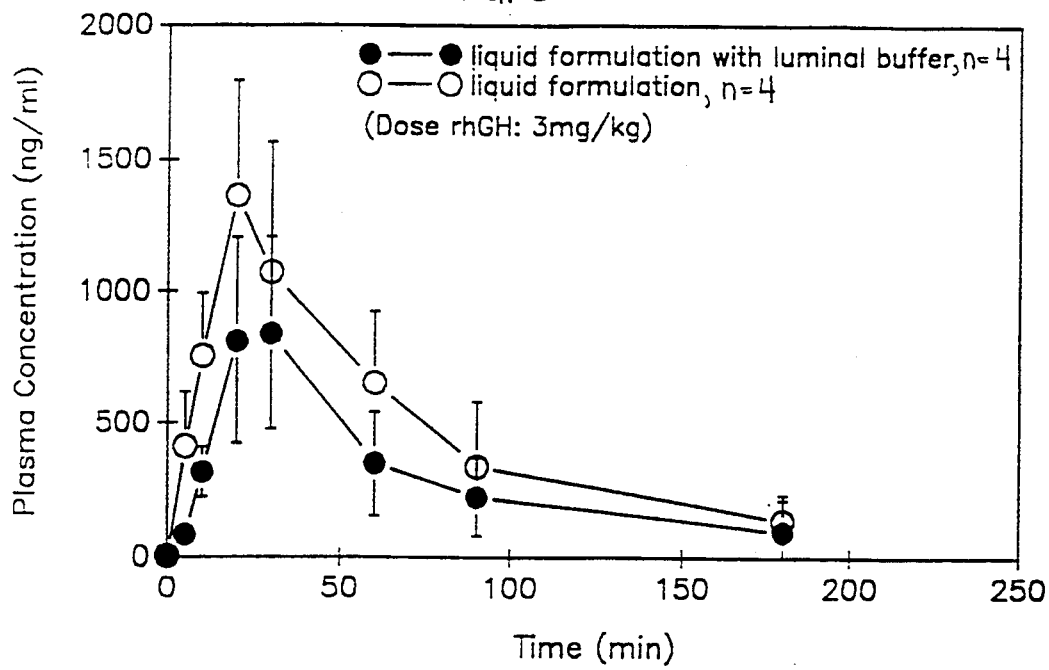
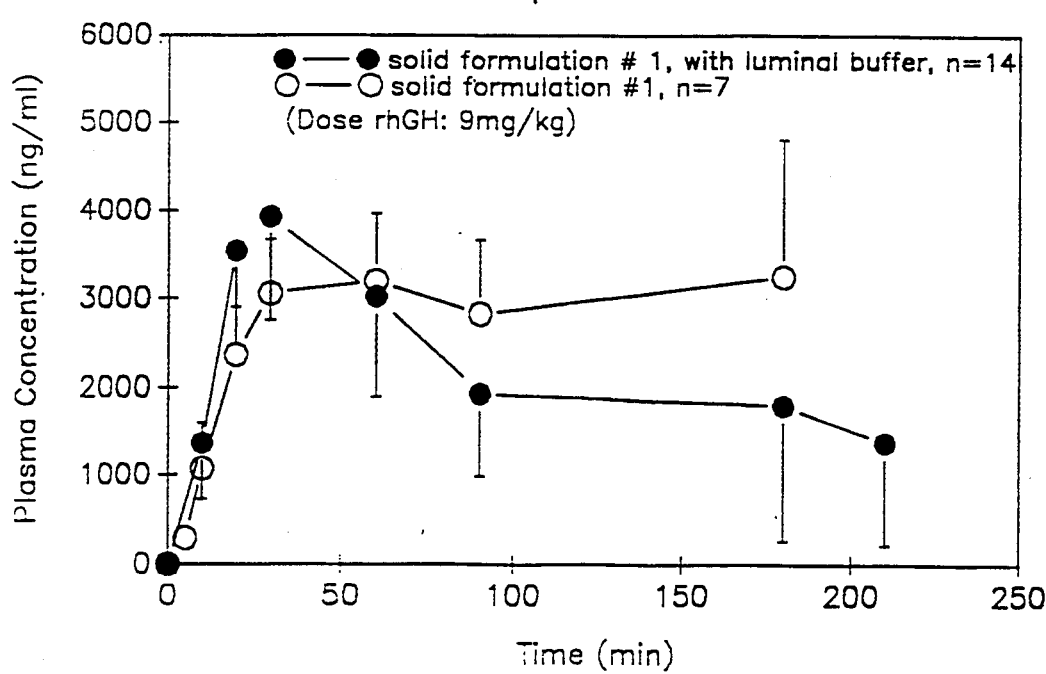

SOLID FORMULATIONS OF THERAPEUTIC PROTEINS FOR GASTROINTESTINAL DELIVERY

FIELD OF THE INVENTION

The present invention relates to compositions of polypeptides, and more particularly to compositions which are solid in nature at room temperature and which provide improved absorption through the wall of the gastrointestinal tract after oral administration.

BACKGROUND OF THE INVENTION

The conventional route of therapy involving protein or peptide drugs is via parenteral administration (i.e., by injection). This is primarily due to the lack of absorption of such drugs through the gastrointestinal tract. However, injections are painful and sometimes difficult to administer relative to other dosage forms. Patient compliance is an important consideration as well since some of these drugs may require frequent administration to juvenile or geriactric patients. Oral delivery is preferable to injections for patient acceptance since it is less painful and more convenient for the patient. However, delivery of therapeutic polypeptides through the gastrointestinal (GI) tract has a number of problems such as low pH in the stomach, proteolytic degradation of the drug in the small intestine, low absorption through the intestinal membrane, and limited stability of such formulations, especially as an aqueous solution, which are all potential barriers to absorption of polypeptides following oral administration.

Recent efforts to deliver polypeptides orally have focused on the use of absorption enhancers. This has led to the discovery that a suspension of sodium salicylate in an excess of an oil can enhance the absorption of human growth hormone from the GI tract (EP publication 177,342; Moore et al., Internat. J. Pharma. 34:35 (1986)). While absorption is improved by this combination, the bioavailability is of only up to about 10-20% of the protein (with reference to intravenous), which is still quite low. As a result, larger amounts of proteins must be administered orally in order to provide the required therapeutic level of protein in the plasma. This is a particular problem with proteins and polypeptides which, even with the advent of biotechnology, are still of relatively limited availability and are complex chemical entities as well, and are very expensive as a result. Additionally, the liquid or semi-solid compositions of the prior art are difficult to formulate or package into a dosage form for oral delivery.

While the above prior art formulations have been found to somewhat improve the absorption of proteins and polypeptides in the colon, they also, as discussed above, have limitations and disadvantages. These limitations and disadvantages are addressed by the present invention.

SUMMARY OF THE INVENTION

Surprisingly, it has now been found that the ratio of sodium salicylate to oil is critical in providing a therapeutic protein/peptide formulation with optimal absorption and bioavailability through the colonic membrane and in providing useful physical characteristics to the formulation. The present invention is directed to a pharmaceutical formulation of a therapeutic polypeptide together with a permeation-enhancing mixture of sodium salicylate and an oil to provide enhanced absorption of the polypeptide through the wall of the gastrointestinal tract after oral administration, the amount of oil being from about 10 wt % to about 30 wt %, preferably from about 15 wt % to about 25 wt %, of the total formulation and the amount of sodium salicylate being from about 70 wt % to about 90 wt %, preferably from about 75 wt % to about 85 wt %, of the total formulation. The polypeptide may be non-lyophilized. The pharmaceutical formulation is characterized as a solid, which provides a convenient and improved format for handling and storage and for the preparation of oral dosage forms (such as pills, capsules and delivery vessels) containing a homogeneous mixture of ingredients.

BRIEF DESCRIPTION OF THE DRAWINGS

FIG. 3 is a graph showing the absorption, in the presence of luminal buffer, of human growth hormone formulated as a prior art liquid suspension.

FIG. 4 is a graph showing the absorption, in the presence of luminal buffer, of human growth hormone formulated as solid granules according to this invention.

DETAILED DESCRIPTION OF THE INVENTION

Figure 1:
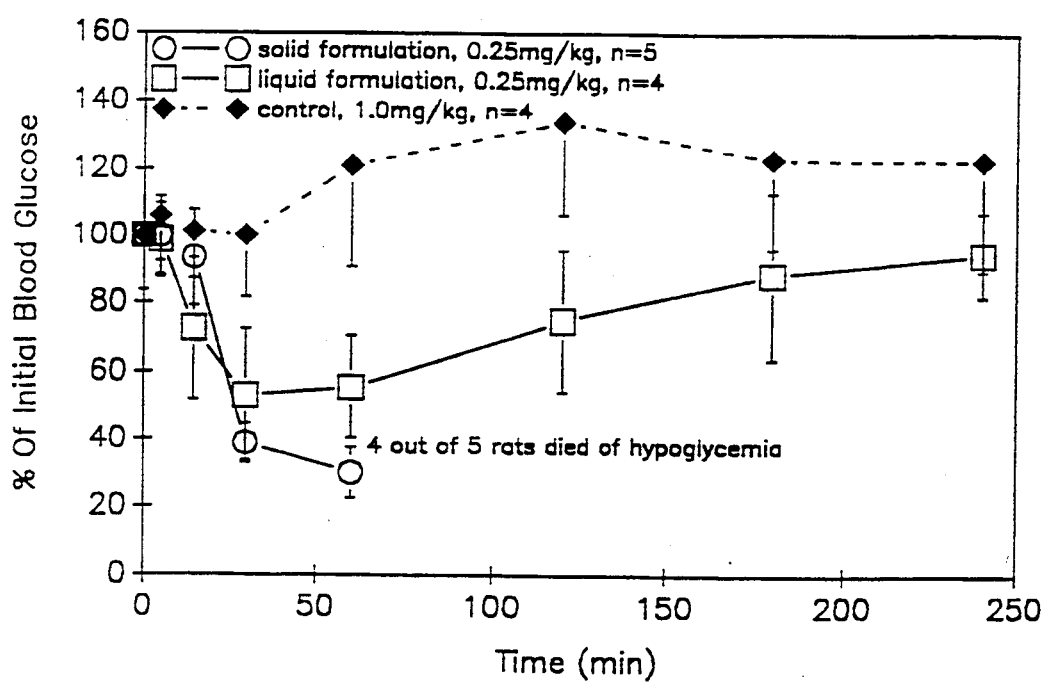
FIG. 1 is a graph showing comparative decrease in the blood glucose levels of fasted anesthetized male rats following administration either of a solid formulation of insulin according to this invention or of a prior art liquid formulation of insulin.

The present invention is applicable to the administration of therapeutic proteins and polypeptides in oral dosage form. The invention surprisingly provides greatly increased absorption through the GI tract and greatly improved bioavailability of the proteins/peptides as compared to that of the prior art formulations. The invention is useful in both human and veterinary therapy and treatment. As used herein and in the appended claims, the term "polypeptide" encompasses proteins and peptides as well as polypeptides within its scope.

The present invention is particularly useful in the administration of polypeptides, including proteins, such as, but not limited to, vaccines, antibodies, antigens, insulin, glucagon, thyroid stimulating hormone, parathyroid and pituitary hormones, calcitonin, renin, prolactin, corticotrophin, thyrotropic hormone, follicle stimulating hormone, chorionic gonadotropin, gonadotropin releasing hormone, bovine somatotropin, porcine somatotropin, oxytocin, vasopressin, prolactin, somatostatin, lypressin, pancreozymin, luteinizing hormone, LHRH, interferons, interleukins, growth hormones such as human growth hormone, bovine growth hormone and porcine growth hormone, fertility inhibitors such as the prostaglandins, fertility promoters, growth factors, human pancreas hormone releasing factor, human tissue plasminogen activator, human tumor necrosis factor, carbohydrates, nucleotides, and the like, and structurally similar bioactive equivalents thereof. By "structurally similar bioactive equivalent" is meant a polypeptide with an amino acid sequence which, although not identical to that of the naturally occurring peptide, is sufficiently similar in structure to produce substantially equivalent therapeutic effects on the subject to that produced by the natural peptide itself. As used herein and in the appended claims, the terms "protein", "peptide" and "polypeptide" refer to both the naturally occurring chemical entities and the structurally similar bioactive equivalents thereof.

Unexpectedly, it has been found that an oral dosage form of a therapeutic polypeptide can be formulated with sodium salicylate and an oil in a particular and critical ratio to provide a substantially increased absorption and bioavailability of the peptide. This ratio additionally provides a formulation, together with the polypeptide, which is a solid. The solid formulation is easy to manipulate in preparing oral dosage forms.

The oil may be chosen from any pharmaceutically acceptable oil including, but not limited to, mineral oil, silicone oil, peanut oil, coconut oil, corn oil, sesame oil, olive oil, fatty acids, vitamin E, and the like. Presently preferred are peanut oil and corn oil.

The amount of oil present in the pharmaceutical formulation is from about 10 wt % to about 30 wt %, preferably from about 15 wt % to about 25 wt %.

The amount of sodium salicylate in the pharmaceutical formulation is from about 70 wt % to about 90 wt %, preferably from about 75 wt % to about 85 wt %.

The amount of therapeutic polypeptide will vary widely, depending on various factors such as the particular peptide to be delivered, the indication to be treated, the individual patient, and the like. The amount will be a therapeutically effective amount, that is, an amount which will provide a therapeutic effect, to be determined in accordance with well-established medical practice.

One potential obstacle to oral administration of the polypeptide is the low gastric pH level and the presence of proteolytic enzymes in the upper GI tract which could inactivate the peptide before it can be absorbed by the intenstinal mucosa. This problem can be solved by the use of enteric coatings which are available for tablets and capsules. Enteric coatings will remain intact in the stomach but will rapidly dissolve once they arrive at the small intestine, thereafter releasing the drug at sites downstream in the intestine (e.g., the ileum and colon). Enteric coatings are well known in the art and are discussed at, for example, *Remington's Pharmaceutical Sciences*, Mack Publishing Co., Easton, Pa.; and *Polymers for Controlled Drug Delivery*, Chapter 3, CRC Press, 1991. Alternatively, a controlled release oral delivery vessel designed to release a drug after a predetermined period of time, and thus after the vessel has passed into the ileum or colon, can be used to deliver the formulation of the present invention. Such vessels include the CHRONSET® delivery device (ALZA Corporation, Palo Alto, Calif.) and the Pulsincap ™ delivery device (R.P. Scherer Co.).

To prepare the pharmaceutical formulation of the present invention, the polypeptide and the sodium salicylate are dry blended together, after which the small amount of oil is added. These materials are mixed together until a homogeneous mixture of ingredients results. The resulting solid formulation can be pressed into tablets which are then coated with a suitable enteric coating. Alternatively, the solid formulation can be placed into a capsule formed of gelatin or the like and coated with an enteric compound, or placed into a controlled release delivery device such as the CHRONSET®. The solid formulation provides a means for easily and conveniently fabricating a dosage form.

The following examples are illustrations of the practice of the present invention, and are intended neither to define nor to limit the scope of the invention in any manner.

In the following examples, an animal model commonly known as the "intracolonic loop model" was employed for testing formulations. In the model, a segment of proximal colon is isolated from a fasted anesthetized male rat, and the colon is ligated at both ends for the segment while a catheter is placed in the lumen and exteriorized above the skin for delivery of test formulation. The colonic contents are flushed out and the colon is returned to the abdomen of the animal. Depending on the experimental set up, the test formulation may be directly added to the loop of colon or added after the loop is filled with 1 mL/kg of 20 mM sodium phosphate buffer, pH 7.9, to more accurately simulate the actual colon environment in a clinical situation. Blood samples are withdrawn from a jugular catheter at prescribed times and the plasma samples are assayed. Since the solid or liquid nature of the formulation depends on the relative amount of sodium salicylate (solid) and oil (liquid) and since the total volume of administrable formulation is limited by the size of the rat colon, direct comparison of solid and liquid formulations with the same amount of sodium salicylate and/or oil is not possible. Therefore, the comparisons were made based upon the same amount of the administered protein drug.

EXAMPLE 1

A solid formulation of insulin according to the present invention was prepared as follows.

Insulin and sodium salicylate were ground into fine powder by passing each of the ingredients separately through an 80 mesh sieve. All procedures were done under amber lighting to prevent possible light-induced degradation of the protein and the sodium salicylate. 0.11 Wt % of the insulin and 73.94 wt % of the sodium salicylate were weighed into a scintillation vial and dry blended using a mechanical roller for 15 min. Peanut oil (25.95 wt %) was then added and the resulting mixture was hand-blended using a spatula for about 15 min, after which the blended paste was removed from the scintillation vial and granulated by passing through a 40 mesh sieve. The granules were then stored in a scintillation vial desiccated at −20° C.

For comparison purposes, an oily suspension formulation based on the prior art was prepared by suspending the appropriate amount of insulin and 40 mg of sodium salicylate into 1 mL of peanut oil.

A comparison was made between the granular formulation of insulin according to this invention and the liquid prior art formulation, both prepared above, using the intracolonic loop model as described previously above. Each of the formulations was tested at the same dose of 0.25 mg/kg of insulin. The plasma samples were assayed for glucose by a glucometer. The results are shown in FIG. 1. The solid formulation induced a substantially bigger drop in the blood glucose after administration of the same amount of insulin as manifested by FIG. 1 and by the hypoglycemic death of 4 out of 5 rats in the study.

EXAMPLE 2

Two solid formulations of human growth hormone (hGH) according to the invention were prepared as follows.

Following the preparation procedures of Example 1, hGH formulations #1 and #2 were prepared, having the following compositions (amounts are in wt %):

|  | Formulation 1 | Formulation 2 |
|---|---|---|
| hGH | 3.75 | 3.75 |
| sodium salicylate | 71.25 | 81.25 |
| peanut oil | 25.0 | 15.0 |

For comparison purposes, an oily suspension formulation based on the prior art was prepared by suspending the appropriate amount of hGH and 40 mg of sodium salicylate into 1 mL of peanut oil.

A comparison was made between the granular formulations #1 and #2 of hGH according to this invention and the liquid prior art formulation, all prepared as above, using the intracolonic loop model as described previously above. The plasma samples were assayed by a double monoclonal radioimmunoassay. The percent bioavailabilities (% BArs) were calculated from the averaged area under the curve (AUC) in reference to the averaged AUC obtained after intravenous injection of a known amount of hGH. These AUC values were calculated from zero to time t. Time t is either the point at which there is no detectable plasma level (90 min for IV experiment) or the time at which blood sampling was stopped (180–240 min for intracolonic experiments). The results are presented in FIGS. 2–5 and Table A.

Figure 2:
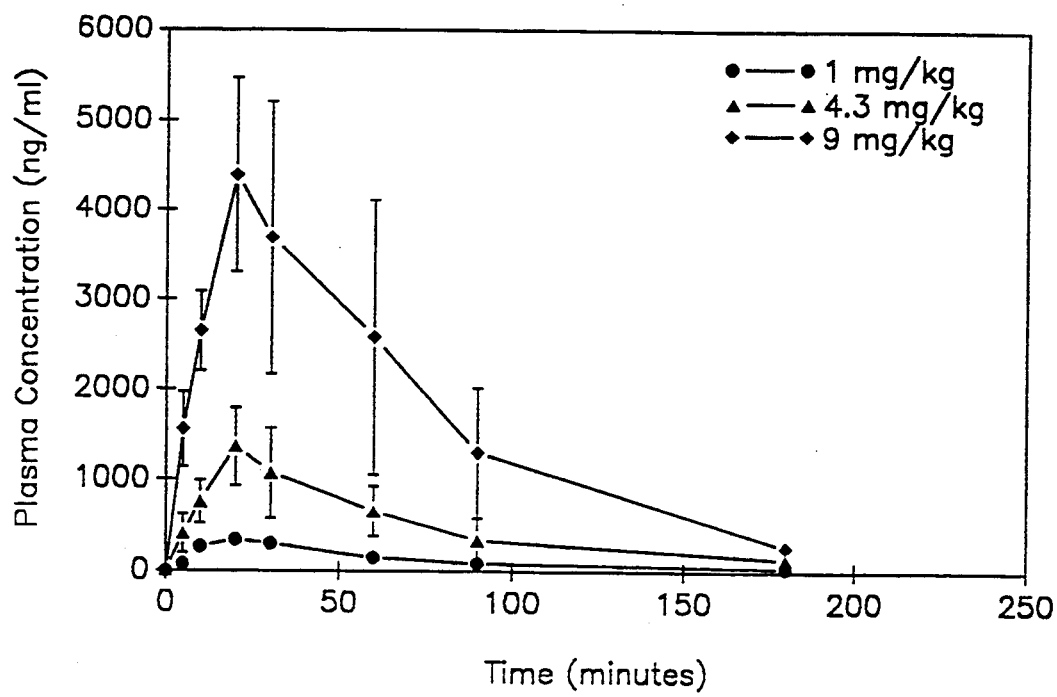
FIG. 2 is a graph showing the absorption of human growth hormone formulated as a liquid suspension according to the prior art.

FIG. 2 shows the absorption of hGH at 1, 4.3 and 9 mg/kg doses when the protein was formulated as oily suspensions of hGH and sodium salicylate in the peanut oil. There is a correspondingly increasing amount of hGH absorbed at higher concentration of hGH in the formulation. However, the relative percent bioavailabilities are constant at 20%.

Luminal buffer decreases the amount of absorption of hGH whether it is in liquid formulation or in solid format. The effect of luminal buffer on the absorption of hGH in liquid formulation is shown in FIG. 3 where a substantial decrease of absorption in the presence of luminal buffer is demonstrated. The dose of hGH for the experiments was 3 mg/kg. The similar decrease of absorption in the presence of luminal buffer for granular formulation is shown in FIG. 4, where 9 mg/kg of hGH was administered.

Figure 5:
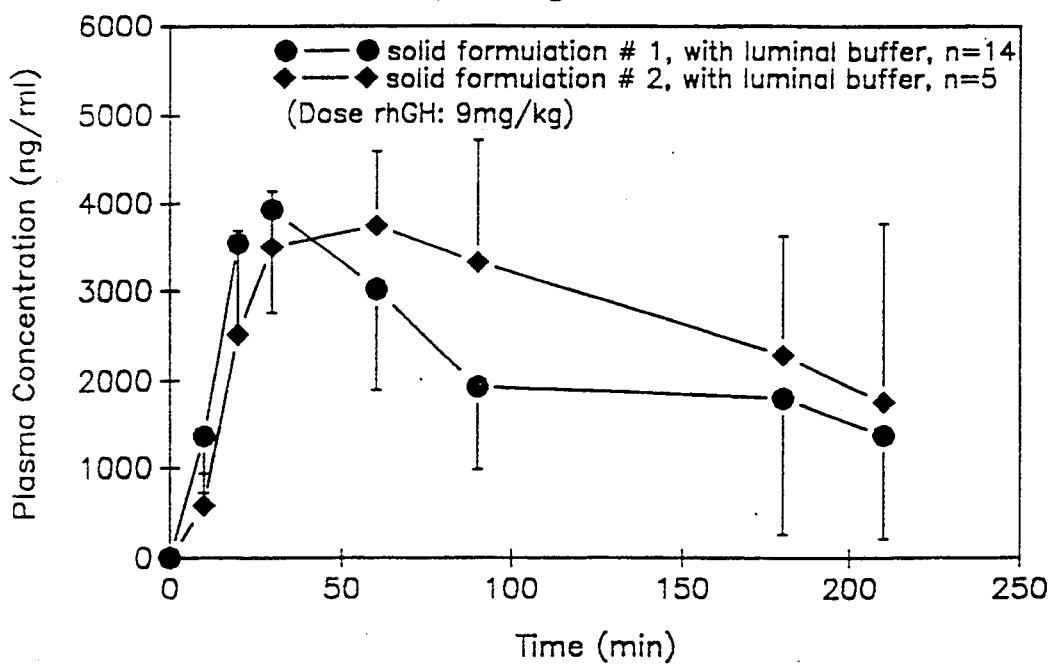
FIG. 5 is a graph showing the absorption profiles, in the presence of luminal buffer, of human growth hormone in two granular formulations according to the invention.

In FIG. 5, the absorption profiles of hGH in the two granular formulations are shown. The granules were delivered in the presence of luminal buffer in the colon. Note the prolonged delivery of hGH in these formulations compared to the absorption from liquid formulations.

A summary of these results are shown in Table A, which demonstrates the superior effectiveness of the solid formulations of the invention. Each BA in the Table is an averaged result of at least four separate animal values. Whether there is a luminal buffer present or not, liquid formulations with excess oil are consistently not as effective as the solid formulations. The relative amounts of sodium salicylate and peanut oil for successful solid formulations are critical; a mere decrease in the amount of oil does not result in a high absorption of hGH. The ineffectiveness of simply increased amount of sodium salicylate in the absence of a certain amount of oil is also clearly demonstrated in the Table.

TABLE A

| hGH (mg/kg) | Na salicylate (mg/kg) | peanut oil (g/kg) | Formulation State | % BA |
|---|---|---|---|---|
| 1 | 40 | 1 | Liquid | 20 |
| 4.3 | 40 | 1 | Liquid | 20 |
| 9 | 40 | 1 | Liquid | 20 |
| 3 | 40 | 0.12 | Liquid | 10 |
| 3 | 40 | 1 | Liquid Luminal Buffer | 14 |
| 9 | 171 | 0.06 | Solid | 52 |
| 9 | 171 | 0.06 | Solid Luminal Buffer | 41 |
| 9 | 195 | 0.04 | Solid Luminal Buffer | 56 |
| 9 | 171 | 0 | Solid Luminal Buffer | <0.1 |

EXAMPLE 3

A solid formulation of hGH was prepared having the same composition as Formulation #2 in Example 2, except that the peanut oil was replaced by corn oil.

Figure 6:
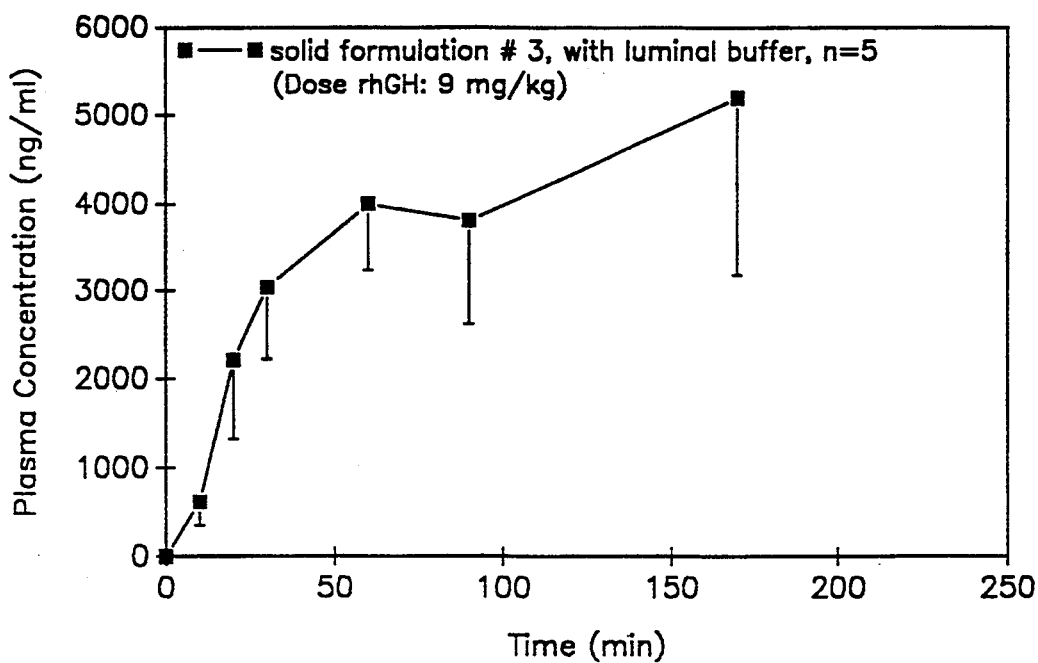
FIG. 6 is a graph showing the absorption profile of human growth hormone in another granular formulation according to this invention.

This formulation was tested in the intracolonic loop model at a dose of 9 mg/kg hGH, and gave a bioavailability of 68% (n=5). FIG. 6 shows the absorption profile.

While this invention has been described with respect to certain specific embodiments thereof, it should not be construed as being limited thereto. Numerous modifications and substitutions will suggest themselves to workers skilled in the art and may be made without departing from the scope of this invention, which is limited only by the following claims.

What is claimed is:

1. A dosage form comprising an orally administrable, enteric-coated capsule wherein said capsule contains (a) a therapeutically effective amount of a peptide selected from the group consisting of human growth hormone and insulin, (b) 70–90 weight % of sodium salicylate, and (c) 10–30 weight % of an oil, such that the bioavailability of said peptide, through the colonic membrane of the gastrointestinal tract, is at least 40%.

2. A method for delivering a peptide, selected from the group consisting of human growth hormone and insulin, through the colonic membrane of the gastrointestinal tract, comprising orally administering the dosage form of claim 1.

3. A dosage form comprising a solid, orally administrable, controlled release delivery formulation wherein said formulation comprises (a) a therapeutically effective amount of a peptide selected from the group consisting of human growth hormone and insulin, (b) 70–90 weight % of sodium salicylate, and (c) 10–30 weight % of an oil, further wherein said solid formulation, subsequent to passage into the colon, releases said peptide to afford a bioavailability of at least 40%.

4. A method for delivering a peptide, selected from the group consisting of human growth hormone and insulin, through the colonic membrane of the gastrointestinal tract, comprising orally administering the dosage form of claim 1.

* * * * *